(12) United States Patent
Ikhlef et al.

(10) Patent No.: US 6,584,167 B1
(45) Date of Patent: Jun. 24, 2003

(54) METHODS AND APPARATUS FOR INCREASING SCANNING MODES

(75) Inventors: Abdelaziz Ikhlef, Waukesha, WI (US); Gregory Zeman, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/133,897

(22) Filed: Apr. 26, 2002

(51) Int. Cl.⁷ .................................................. A61B 6/03
(52) U.S. Cl. ............................ 378/19; 378/4; 378/901
(58) Field of Search ........................ 378/4, 8, 15, 19, 378/901

(56) References Cited

U.S. PATENT DOCUMENTS

| | | | |
|---|---|---|---|
| 5,519,450 A | * | 5/1996 | Urbanus et al. ............ 348/600 |
| 5,534,772 A | | 7/1996 | Rogers |
| 5,822,544 A | | 10/1998 | Chaco et al. |
| 6,023,661 A | | 2/2000 | Sottery |
| 6,038,380 A | | 3/2000 | Wise et al. |
| 6,292,919 B1 | | 9/2001 | Fries et al. |
| 6,433,835 B1 | | 8/2002 | Hartson et al. |
| 2002/0059312 A1 | * | 5/2002 | Ishii ........................ 707/200 |

* cited by examiner

Primary Examiner—David V. Bruce
(74) Attorney, Agent, or Firm—Carl B. Horton, Esq.; Armstrong Teasdale LLP

(57) ABSTRACT

A method for transmitting a scan mode to an imaging system includes loading a least significant nibble into a first latch register and loading a most significant nibble into a second latch register such that a byte of information is received at a decoder.

24 Claims, 3 Drawing Sheets

METHODS AND APPARATUS FOR INCREASING SCANNING MODES

BACKGROUND OF THE INVENTION

This invention relates generally to computed tomographic (CT) imaging, and more particularly to manufacturing a detector array for increasing scanning modes using the CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In some known CT imaging system configurations, the detector includes a plurality of modules including a scintillator array and a photodiode array. The photodiodes are coupled to a switching apparatus which includes an array of switching devices such as field effect transistors (FETs) that control the combination of photodiode outputs based on the desired number of slices and slice thickness input by an operator. The photodiode outputs are supplied to a Data Acquisition System (DAS), via the FETs using a connector such as a flex cable. One known imaging system includes a flex cable including six detector control lines connected to the FETs to address sixty-four scanning modes. In order to address a greater quantity of medical modes, a greater quantity of scanning modes is required.

BRIEF DESCRIPTION OF THE INVENTION

A method for transmitting a scan mode to an imaging system is provided. The method includes loading a least significant nibble into a first latch register and loading a most significant nibble into a second latch register such that a byte of information is received at a decoder.

A method for transmitting a scan mode to an imaging system is provided. The method includes connecting an electrical cable including n data lines to a decoder and multiplexing the n data lines such that the decoder is operable in $2^{2n}$ modes.

A detector module for a computed tomographic imaging system assembly is provided. The module includes a scintillator array including a plurality of scintillation elements, a photodiode array including a plurality of photodiodes optically coupled to the scintillator array, a decoder coupled to the photodiode array, the decoder including a plurality of latch registers, and a flexible cable electrically connected to the decoder assembly and configured to transmit signals representative of a light output by the scintillator array to the CT imaging system.

A computed tomographic (CT) imaging system is provided. The imaging system includes a detector array including a plurality of modules wherein each module includes a scintillator array including a plurality of scintillation elements, a photodiode array including a plurality of photodiodes optically coupled to the scintillator array, a decoder coupled to the photodiode array, the decoder including a plurality of latch registers, and a flexible cable electrically connected to the decoder assembly, the cable including n data lines, at least one radiation source, and a computer coupled to the detector array and radiation source and configured to multiplex the n data lines such that the decoder is operable in $2^{2n}$ modes.

A computer readable medium encoded with a program executable by a computer for transmitting a scan mode to an imaging system is provided. The program is configured to instruct the computer to transmit a chip enable signal to a first latch register and a second latch register and transmit a chip select signal to said the first latch register and the second latch register such that a byte of information is received at a decoder.

DETAILED DESCRIPTION OF THE INVENTION

In some known CT imaging system configurations, an x-ray source and a detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view", A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan for a single slice CT. For multi-slice CT, multiple helixes are generated from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
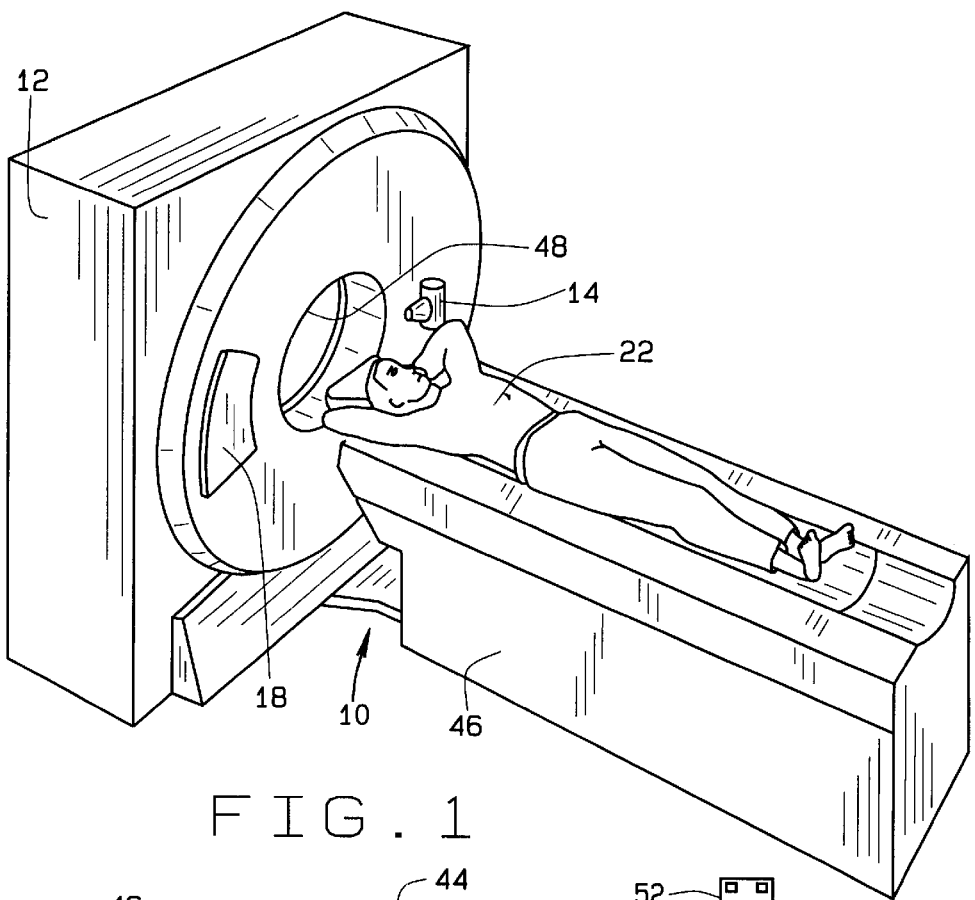
FIG. 1 is a pictorial view of a CT imaging system.
Figure 2:
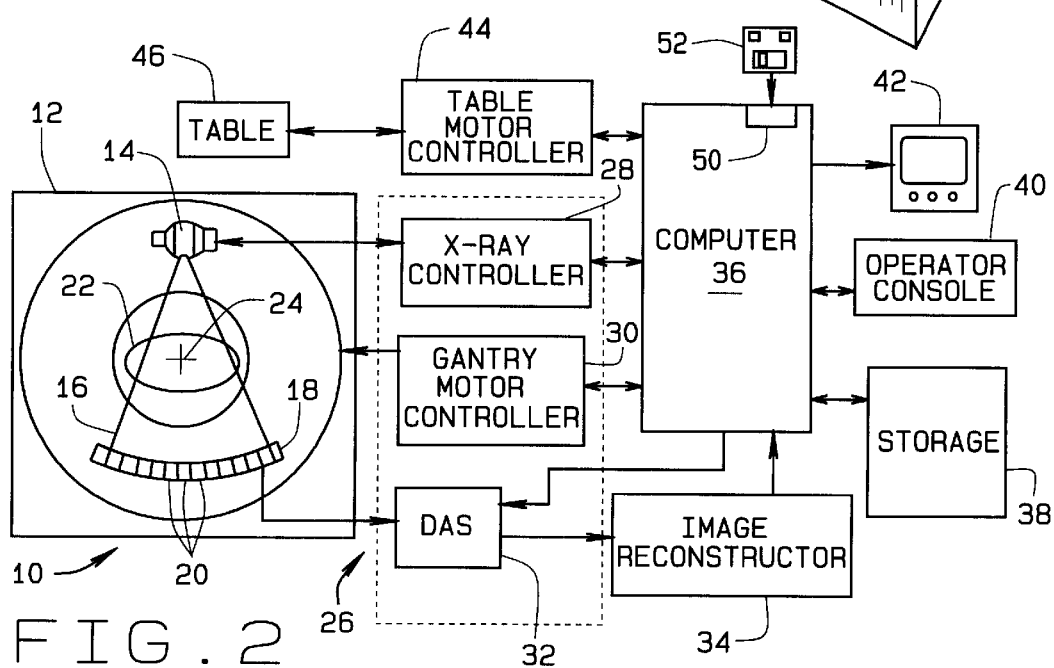
FIG. 2 is a block schematic diagram of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data received from detector elements 20 through a flex cable 33, and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figures 3, 4:
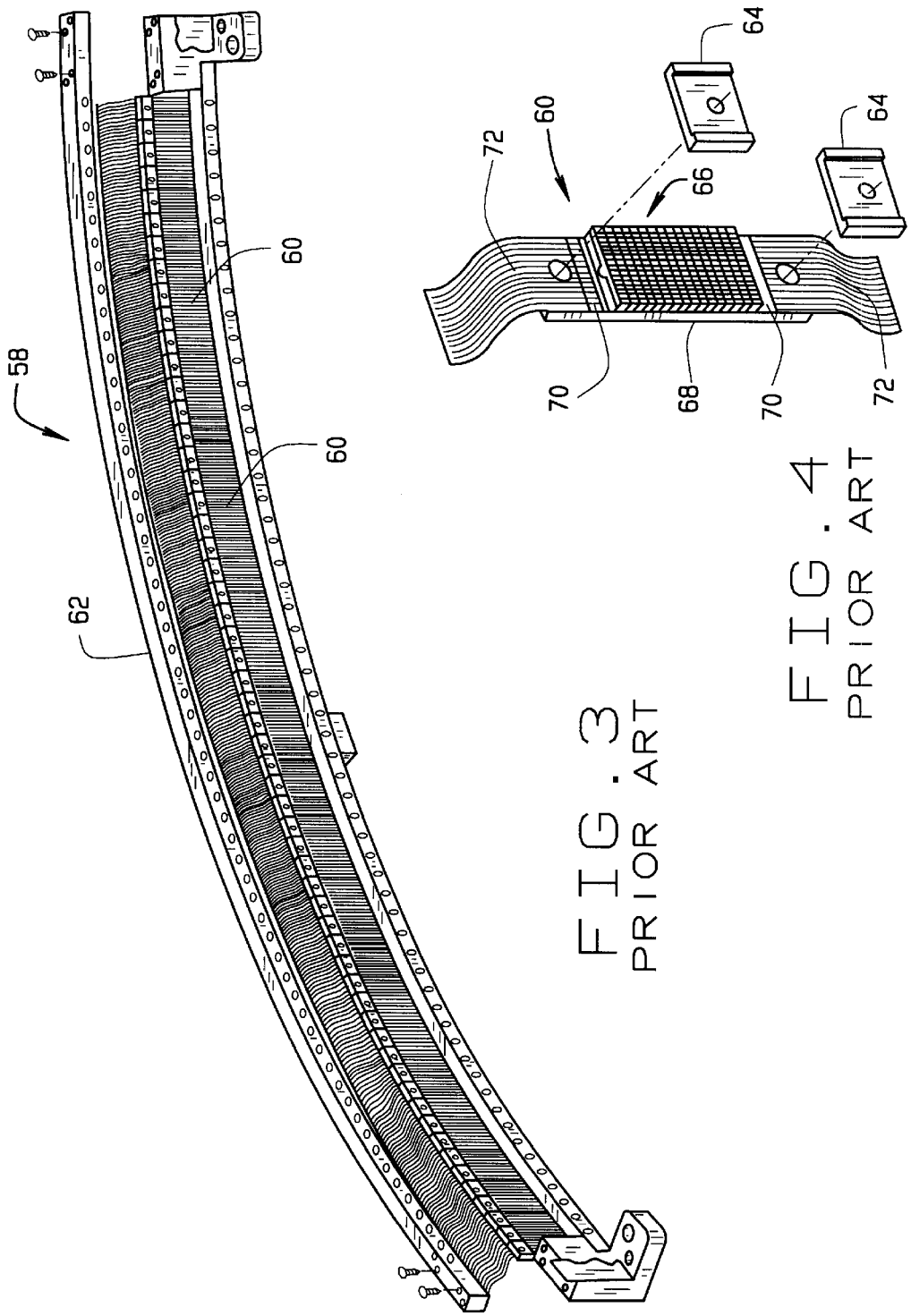
FIG. 3 is a prior art view of a detector array.
FIG. 4 is a prior art view of a module used in the detector array in FIG. 3.

FIG. 3 is a prior art figure of a detector array 58 that includes a plurality of modules 60. FIG. 4 is a prior art figure of a module 60 used in detector array 58. Imaging arrays typically include a photosensor array coupled to a scintillating medium. Radiation absorbed in the scintillator generates optical photons which in turn pass into a photosensor, such as a photodiode. The photon is absorbed in the photosensor and an electrical signal corresponding to an incident photon flux is generated. Hydrogenated amorphous silicon (a-Si:H) is commonly used in the fabrication of photosensors due to advantageous photoelectric characteristics of a-Si:H and a relative ease of fabricating such devices. In particular, photosensitive elements, such as photodiodes, can be formed in connection with necessary control or switching elements, such as thin film transistors (TFTs), in a relatively large array. Radiation detectors and display arrays are typically fabricated on a large substrate on which many components, including TFTs, address lines, capacitors, and devices such as photosensors, are formed through the deposition and patterning of layers of conductive, semiconductive, and insulative materials.

Each detector module 60 is secured to a detector housing 62 by plates 64. Each module 60 includes a multidimensional scintillator array 66 and a high density semiconductor array (not visible). Scintillator array 66 includes a plurality of scintillation elements arranged in an array, and the semiconductor array includes a plurality of photodiodes arranged in an identical array. The photodiodes are deposited, or formed, on a substrate 68, and scintillator array 66 is positioned over and secured to substrate 68.

A switch and decoder apparatus 70 is coupled to the photodiode array. The photodiodes are optically coupled to scintillator array 66 and include electrical output lines for transmitting signals representative of the light output by scintillator array 66. Particularly, each photodiode produces a separate low level analog output signal that is a measurement of the beam attenuation for a specific scintillator of scintillator array 66. The photodiode output lines extend from opposing sides of the semiconductor, or photodiode array and are connected (e.g., wire bonded) to respective decoder 70.

Decoder 70 is a multidimensional semiconductor switch array of similar width size as the photodiode array. Decoder 70 is electrically connected to the semiconductor array and DAS 32 (shown in FIG. 2). Decoder 70 includes a plurality of field effect transistors (FETs) arranged as a multidimensional array. Each FET includes an input line electrically connected to one of the respective photodiode output lines, an output line, and a control line (not shown). FET output and control lines are electrically connected to DAS 32 via a flexible electrical cable 72. Specifically, approximately one-half of the photodiode output lines are electrically connected to each FET input line on a first side of the array, and the other approximately one-half of the photodiode output lines are electrically connected to the FET input lines on a second side of the array.

Figure 5:
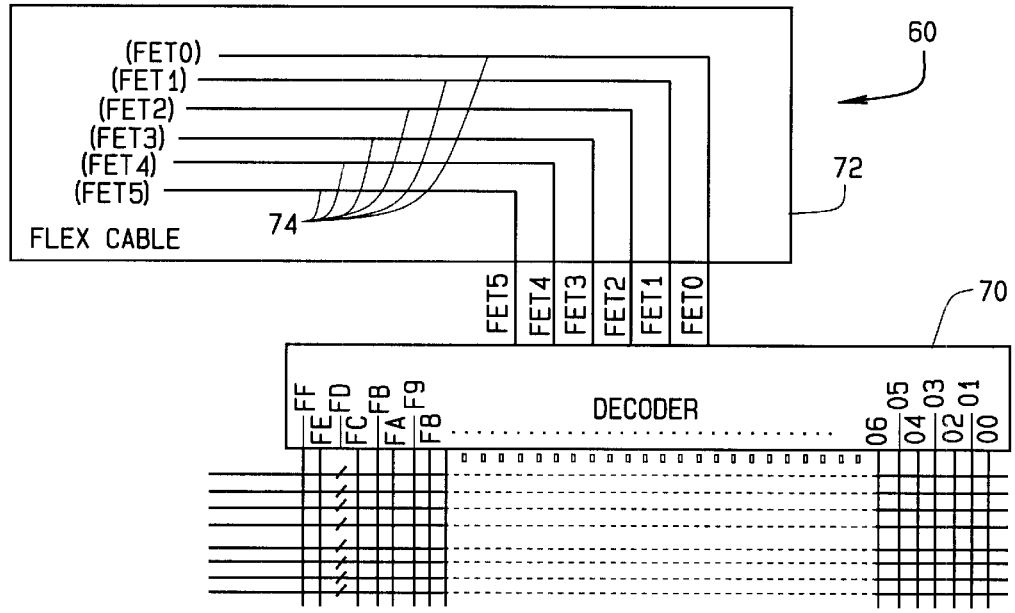
FIG. 5 is a prior art view of a portion of a module shown in FIG. 4.

FIG. 5 is a prior art view of a portion of detector module 60 shown in FIG. 4. Detector module 60 includes decoder 70 and flexible electrical cable 72. Cable 72 includes a plurality of decoder control lines 74 electrically connected to decoder 70 to address sixty-four FET modes and therefore facilitate enabling sixty-four different operating modes. As shown cable 72 includes six decoder control lines 74, and is therefore capable of addressing 64 operating modes, i.e. ($2^6$=64).

Figure 6:
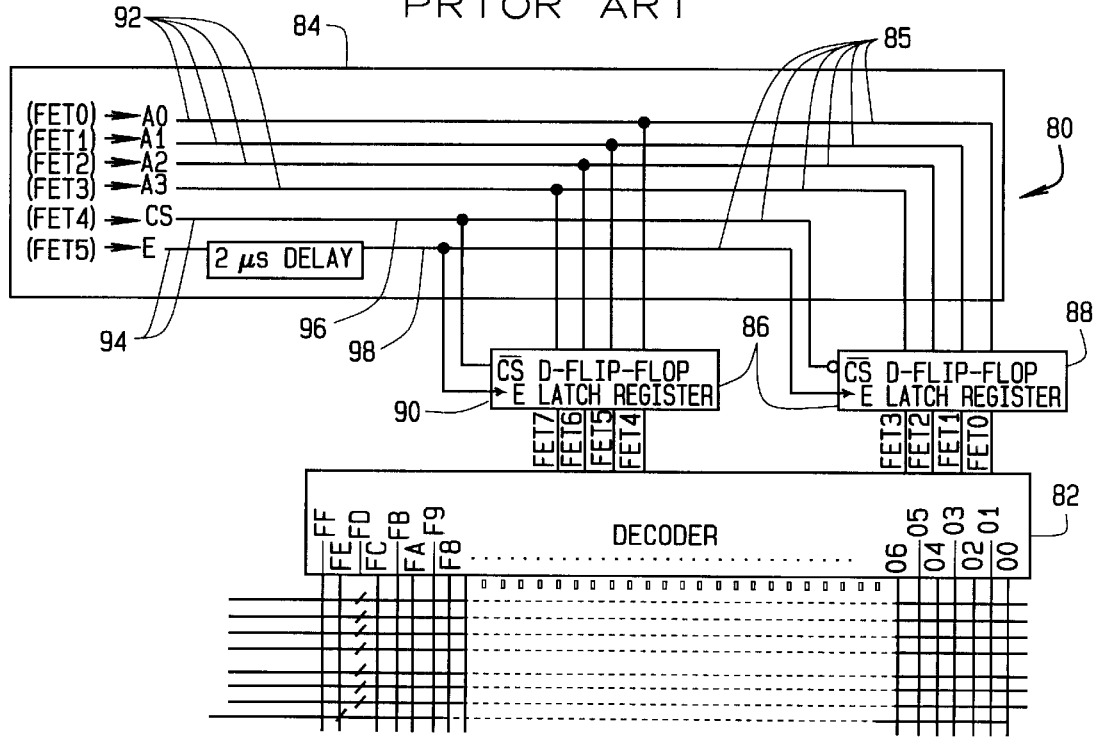
FIG. 6 is a view of a module used in the detector array in FIG. 1.

FIG. 6 is a detector module 80 formed with detector 18 that is used with imaging system 10 (shown in FIG. 1). Detector module 80 includes a decoder 82 and a flexible electrical cable 84 including a plurality of decoder control lines 85. In the exemplary embodiment, flexible electrical cable include six decoder control lines 85. Detector module 80 also includes a plurality of latch registers 86, such as, but not limited to, a first latch register 88 and a second latch register 90 wherein first latch register 88 and second latch register 90 are based on D-Flip-Flop latch registers. In one embodiment, first latch register 88 and second latch register 90 are formed integrally with decoder 82. In another embodiment, first latch register 88 and a second latch register 90 are unitary components electrically connected to decoder 82 and cable 84. Decoder control lines 85 include n data lines 92 and two latch register control lines 94 electrically coupled to first latch register 88 and second latch register 90. In the exemplary embodiment decoder control lines 85 include n=4 data lines 92 capable of addressing $2^{2n}$ scan modes. Decoder control lines 85 also include m latch register control lines 94 electrically coupled to first latch register 88 and second latch register 90. In the exemplary embodiment, decoder control lines 85 include m=2 latch register control lines 94. In one embodiment, latch register control lines 94 include a chip select line (CS) 96 and a chip enable line (E) 98. First latch register 88 and second latch register 90 each include four outputs respectively that are input to decoder 82.

Decoder 82 controls the operation of the FETs to enable, disable, or combine photodiode outputs in accordance with a desired number of slices and slice resolutions for each slice. Decoder 80, in one embodiment, is a decoder chip or a FET controller and includes a plurality of output and control lines coupled to the FETs and DAS 32. The outputs from decoder 82 are electrically connected to the switch apparatus control lines to enable the FETs to transmit the proper data. Decoder control lines 74 are electrically connected to the FET control lines and determine which of the outputs will be enabled. Utilizing decoder 80, specific FETs are enabled, disabled, or have their outputs combined such that specific photodiode outputs are electrically connected to DAS 32.

In one embodiment, detector 18 includes fifty-seven modules 80. The semiconductor array and scintillator array 66 each have an array size of approximately sixteen by sixteen. As a result, detector 18 has sixteen rows and nine hundred and twelve columns, i.e. sixteen multiplied by fifty-seven modules, which enables sixteen simultaneous slices of data to be collected with each rotation of gantry 12 (shown in FIG. 1). Also, detector 18 may be operated in many different slice thickness and number modes, e.g., one, two, and four slice modes. For example, the FETs can be configured in the eight slice mode such that data is collected for eight slices from one or more rows of the photodiode array. Depending upon the specific configuration of the FETs as defined by decoder control lines 85, various combinations of photodiode outputs can be enabled, disabled, or combined so that the slice thickness may, for example, be 1.25 mm, 2.5 mm, 3.75 mm, or 5 mm. Additional examples include, a single slice mode including one slice with slices ranging from 1.25 mm thick to 20 mm thick, and a two slice mode including two slices with slices ranging from 1.25 mm thick to 10 mm thick. Of course, many other modes are possible.

The detector module 80 system and its associated latched addressing modes described herein are offered by way of illustration rather than limitation, and it is appreciated that the specific quantity and type of latch registers can be modified or increased in a wide variety of detector modules due to a specific quantity of a scan mode requirements without departing from the scope and spirit of the instant invention. For ease of illustration and not as a limitation only two latch registers, four address lines, a single chip select line, and a single latch enable line have been described.

A scan mode selection includes using the (A0–A3) bus to load a less significant nibble (FET0–FET3), and using the (A0–A3) bus to load a most significant nibble (FET 4–FET 7), wherein nibble as used herein refers to four bits or one-half a byte. In the exemplary embodiment, decoder 82 can address 8 FET lines using six decoder control lines 85 to address 256 scanning modes.

In use, when chip select line 96 is set to low, i.e. a signal is not transmitted to either latch register 88 or latch register 90, and chip enable line 98 is set to high, the least significant (LS) nibble (FET0–FET3) of the scan mode address is loaded into decoder 82. This corresponds to the hexadecimal word 1X, where X is the mode address LS nibble. When chip select line 96 is set to high, i.e. a signal is transmitted to latch register 88 and latch register 90, and chip enable line 98 is set to high, the most significant nibble (FET4–FET7), corresponding to the hexadecimal word 3X, where X is the mode address MS nibble, of the scan mode address is loaded into decoder 82. In one embodiment, the latch enable is delayed by approximately 2 microsecond to facilitate transferring the mode address into the decoder inputs.

The design of FET chip mode decoder 82 including latched registers 86 facilitates achieving a higher number of slice modes without changing the current interface architecture of CT imaging system 10 including the flex cable, the data acquisition system (DAS), the connectors and the diode-detector interface. For example, at least one known imaging system uses six decoder control lines (FET0–FET5) in order to address 64 modes. In order to address a higher number of medical applications, a higher number of scanning modes and combinations is desirable. Therefore, one will need to have more than six decoder control lines to address the new FET modes. In the exemplary embodiment, a mode selection control line reduction using a latched multiplexing of decoder control lines 85 facilitates a scalable mode selection by trading Chip Select and nibble word width. Multiplexing also facilitates a reduction in operating electrical noise immunity of mode selection using Latch Enable protection of entered mode while increasing the scan modes from 64 to at least 256.

While the invention has been described in terms of various specific embodiments, those skilled in the art will recognize that the invention can be practiced with modification within the spirit and scope of the claims.

What is claimed is:

1. A method for transmitting a scan mode to an imaging system, said method comprising:

loading a least significant nibble into a first latch register; and loading a most significant nibble into a second latch register such that a byte of information is received at a decoder.

2. A method in accordance with claim 1 further comprising:

transmitting a chip enable signal to the first latch register and the second latch register; and transmitting a chip select signal to the first latch register and the second latch register.

3. A method in accordance with claim 2 wherein said transmitting a chip enable signal to the first latch register and the second latch register further comprises transmitting a chip enable signal to the first latch register and the second latch register approximately two microseconds after transmitting a chip select signal to the first latch register and the second latch register.

4. A method in accordance with claim 1 wherein said loading a least significant nibble into a first latch register comprises loading a least significant nibble into a first latch register configured to transmit data to a decoder when a chip select line is set to low and a chip enable line is set to high.

5. A method in accordance with claim 1 wherein said loading a most significant nibble into a second latch register comprises loading a most significant nibble into a second latch register configured to transmit data to a decoder when a chip select line is set to high and a chip enable line is set to high.

6. A method for transmitting a scan mode to an imaging system, said method comprising:
   loading a least significant nibble into a first latch register including a D-Flip-Flop latch register configured to transmit data to a decoder when a chip select line is set to low and a chip enable line is set to high;
   loading a most significant nibble into a second latch register configured to transmit data to a decoder when a chip select line is set to high and a chip enable line is set to high.

7. A method for transmitting a scan mode to an imaging system, said method comprising:
   connecting an electrical cable including n data lines to a decoder; and
   multiplexing the n data lines such that the decoder is operable in $2^{2n}$ modes.

8. A method in accordance with claim 7 wherein said multiplexing the n data lines comprises:
   loading a least significant nibble into a first latch register; and
   loading a most significant nibble into a second latch register such that a byte of information is received at the decoder.

9. A method in accordance with claim 8 wherein said loading a least significant nibble into a first latch register comprises loading a least significant nibble into a first latch register when a chip select signal is set to low and a chip enable signal is set to high, and said loading a most significant nibble into a second latch register comprises loading a most significant nibble into a second latch register when the chip select signal is set to high and the chip enable signal is set to high.

10. A method in accordance with claim 9 wherein said loading a least significant nibble into a first latch register comprises loading a least significant nibble into a first latch register configured to transmit data to a decoder, and loading a most significant nibble into a second latch register comprises loading a most significant nibble into a second latch register configured to transmit data to the decoder.

11. A method in accordance with claim 9 wherein said loading a least significant nibble into a first latch register when a chip select signal is set to low and a chip enable signal is set to high, and said loading a most significant nibble into a second latch register when the chip select signal is set to high and the chip enable signal is set to high comprises transmitting the chip enable signal to the first latch register and the second latch register approximately two microseconds after transmitting the chip select signal to the first latch register and the second latch register.

12. A detector module for a computed tomographic imaging system assembly, said module comprising:
   a scintillator array comprising a plurality of scintillation elements;
   a photodiode array comprising a plurality of photodiodes optically coupled to said scintillator array;
   a decoder coupled to said photodiode array, said decoder comprising a plurality of latch registers; and
   a flexible cable electrically connected to said decoder assembly and configured to transmit signals representative of a light output by said scintillator array to said CT imaging system.

13. A detector in accordance with claim 12 wherein said electrical cable comprises exactly six decoder control lines electrically connected to said latch registers, wherein said six decoder control lines comprise two latch register control lines and four data lines.

14. A detector in accordance with claim 13 wherein said latch register control lines comprise a chip select line and a chip enable line.

15. A detector in accordance with claim 12 wherein said plurality of latch registers comprises a first latch register comprising a D-Flip-Flop latch register, a second latch register comprising a D-Flip-Flop latch register.

16. A computed tomographic (CT) imaging system, said imaging system comprising:
   a detector array comprising a plurality of modules wherein each said module comprises:
      a scintillator array comprising a plurality of scintillation elements;
      a photodiode array comprising a plurality of photodiodes optically coupled to said scintillator array;
      a decoder coupled to said photodiode array, said decoder comprising a plurality of latch registers; and
      a flexible cable electrically connected to said decoder assembly, said cable comprising n data lines;
   at least one radiation source; and
   a computer coupled to said detector array and radiation source and configured to:
      multiplex said n data lines such that said decoder is operable in $2^{2n}$ modes.

17. A CT imaging system in accordance with claim 16 wherein to multiplex said n data lines such that said decoder is operable in $2^{2n}$ modes, said computer further configured to transmit a chip enable signal to a first latch register and a second latch register approximately two microseconds after transmitting a chip select signal to said first latch register and said second latch register.

18. A CT imaging system in accordance with claim 16 wherein to multiplex said n data lines such that said decoder is operable in $2^{2n}$ modes, said computer further configured to set a chip select line to low and set a chip enable line to high to load a least significant nibble into said first latch register.

19. A CT imaging system in accordance with claim 16 wherein to multiplex said n data lines such that said decoder is operable in $2^{2n}$ modes, said computer further configured to set a chip select line to high and set a chip enable line to high to load a most significant nibble into said second latch register.

20. A CT imaging system in accordance with claim 17 wherein to transmit a chip enable signal to said first latch register and said second latch register, said computer further configured to transmit a chip enable signal to said first latch register and said second latch register approximately two microseconds after transmitting a chip select signal to said first latch register and said second latch register.

21. A computer readable medium encoded with a program executable by a computer for transmitting a scan mode to an imaging system, said program configured to instruct the computer to:

transmit a chip enable signal to a first latch register and a second latch register; and transmit a chip select signal to said first latch register and said second latch register such that a byte of information is received at a decoder.

22. A computer readable medium in with claim 21 wherein to transmit a chip enable signal to said first latch register and said second latch register, said program further configured to transmit a chip enable signal to said first latch register and said second latch register approximately two microseconds after transmitting a chip select signal to said first latch register and said second latch register.

23. A computer readable medium in with claim 21 wherein to load a least significant nibble into said first latch register, said program further configured to set a chip select line to low and set a chip enable line to high to load a least significant nibble into said first latch register.

24. A computer readable medium in with claim 21 wherein to load a most significant nibble into said second latch register, said program further configured to set a chip select line to high and set a chip enable line to high to load a most significant nibble into said second latch register.

* * * * *